(12) United States Patent
Caplice

(10) Patent No.: US 11,678,967 B2
(45) Date of Patent: Jun. 20, 2023

(54) INTRAVASCULAR CELL THERAPY DEVICE

(71) Applicant: University College Cork—National University of Ireland, Cork, Mallow (IE)

(72) Inventor: Noel Caplice, Mallow (IE)

(73) Assignee: Provasctec Limited, Galway (IE)

( * ) Notice: Subject to any disclaimer, the term of this patent is extended or adjusted under 35 U.S.C. 154(b) by 0 days.

(21) Appl. No.: 16/489,601

(22) PCT Filed: Feb. 28, 2018

(86) PCT No.: PCT/EP2018/054922
§ 371 (c)(1),
(2) Date: Aug. 28, 2019

(87) PCT Pub. No.: WO2018/158311
PCT Pub. Date: Sep. 7, 2018

(65) Prior Publication Data
US 2020/0015953 A1 Jan. 16, 2020

(30) Foreign Application Priority Data
Feb. 28, 2017 (EP) ..................... 17158548

(51) Int. Cl.
*A61F 2/06* (2013.01)
*A61L 27/54* (2006.01)
(Continued)

(52) U.S. Cl.
CPC ................ *A61F 2/022* (2013.01); *A61F 2/06* (2013.01); *A61L 27/44* (2013.01); *A61L 27/507* (2013.01);
(Continued)

(58) Field of Classification Search
CPC .... A61F 2/022; A61F 2/04; A61F 2/06; A61F 2/07; A61F 2/82; A61F 2210/0004;
(Continued)

(56) References Cited

U.S. PATENT DOCUMENTS 3,976,071 A 8/1976 Sadek
4,832,686 A 5/1989 Anderson
(Continued)

FOREIGN PATENT DOCUMENTS

EP 3056562 A1 8/2016
WO 02/056790 A2 7/2002
WO 2014141226 A1 9/2014

OTHER PUBLICATIONS

Kumar, A. H.S. et al., "Intravascular cell delivery device for therapeutic VEGF-induced angiogenesis in chronic vascular occlusion," Biomaterials, vol. 35, pp. 9012-9022 (2014).
(Continued)

*Primary Examiner* — Dinah Baria
(74) *Attorney, Agent, or Firm* — Bookoff McAndrews, PLLC

(57) ABSTRACT

An intravascular cell therapy device comprises a scaffold (2, 12) that is radially adjustable between a contracted orientation suitable for transluminal delivery to a vascular locus and an expanded orientation, and a biodegradable matrix provided on at least a portion of the scaffold that is suitable for seeding with cells and degrades in a vascular environment. The scaffold is configured to have a distal piercing tip (5) when in a deployed orientation. The scaffold comprises a plurality of sidewall panels (3, 13, 14) arranged around a longitudinal axis of the scaffold, and adjustable couplings (4) between the panels configured for adjustment between an
(Continued)

expanded configuration and a contracted orientation, and in which each sidewall panel comprises a matrix suitable for seeding with cells.

23 Claims, 8 Drawing Sheets

(51) Int. Cl.
*A61F 2/02* (2006.01)
*A61L 27/44* (2006.01)
*A61L 27/50* (2006.01)
*A61L 27/58* (2006.01)
*A61F 2/848* (2013.01)

(52) U.S. Cl.
CPC ............... *A61L 27/54* (2013.01); *A61L 27/58* (2013.01); *A61F 2002/8486* (2013.01); *A61F 2210/0004* (2013.01); *A61F 2230/0023* (2013.01); *A61F 2230/0067* (2013.01); *A61F 2230/0069* (2013.01); *A61F 2250/0067* (2013.01); *A61L 2300/64* (2013.01)

(58) Field of Classification Search
CPC ...... A61F 2230/0069; A61F 2230/0023; A61F 2230/0067; A61F 2250/0067; A61F 2002/8486; A61L 27/58; A61L 27/44; A61L 27/54; A61L 27/507; A61L 2300/64; A61B 5/6876; A61B 5/6862; A61M 29/00
See application file for complete search history.

(56) References Cited

U.S. PATENT DOCUMENTS

| | | |
|---|---|---|
| 4,883,666 A | 11/1989 | Sabel et al. |
| 4,894,231 A | 1/1990 | Moreau et al. |
| 4,897,268 A | 1/1990 | Tice et al. |
| 5,176,907 A | 1/1993 | Leong |
| 5,447,724 A | 9/1995 | Helmus et al. |
| 5,464,650 A | 11/1995 | Berg et al. |
| 5,484,584 A | 1/1996 | Wallace et al. |
| 5,543,158 A | 8/1996 | Gref et al. |
| 5,569,463 A | 10/1996 | Helmus et al. |
| 5,609,629 A | 3/1997 | Fearnot et al. |
| 5,624,411 A | 4/1997 | Tuch |
| 5,656,297 A | 8/1997 | Bernstein et al. |
| 5,824,049 A | 10/1998 | Ragheb et al. |
| 5,876,452 A | 3/1999 | Athanasiou et al. |
| 5,879,808 A | 3/1999 | Wary et al. |
| 5,925,037 A | 7/1999 | Guglielmi et al. |
| 6,051,276 A | 4/2000 | Wary et al. |
| 6,054,122 A | 4/2000 | MacPhee et al. |
| 6,096,070 A | 8/2000 | Ragheb et al. |
| 6,197,013 B1 * | 3/2001 | Reed .................. A61F 2/86 604/509 |
| 6,855,160 B1 | 2/2005 | Gambale et al. |
| 2002/0165479 A1 | 11/2002 | Wilk |
| 2005/0096731 A1 | 5/2005 | Looi et al. |
| 2007/0104695 A1 | 5/2007 | Quijana et al. |
| 2008/0138378 A1 * | 6/2008 | Looi ............. A61L 31/088 424/423 |
| 2009/0227026 A1 * | 9/2009 | Rapoport ............ A61F 2/06 156/196 |
| 2015/0086607 A1 * | 3/2015 | Johnson ........... A61L 31/148 424/426 |
| 2015/0112419 A1 | 4/2015 | Ahn et al. |
| 2016/0166257 A1 | 6/2016 | Allen et al. |
| 2017/0151049 A1 * | 6/2017 | La Francesca ......... A61L 27/18 |

OTHER PUBLICATIONS

O'Brien, F. J., "Biomaterials & scaffolds for tissue engineering," Materials Today, vol. 14, issue 3, pp. 88-95 (Mar. 2011).
Alrefai, M. T., "Cardiac tissue engineering and regeneration using cell-based therapy," Stem Cells and Cloning: Advances and Applications, vol. 8, pp. 81-101 (2015).
Electrospin Tech, "Introduction to Nanofiber Covered Stent," last updated: Jan. 26, 2021—http://electrospintech.com/coveredstent.html#.WJh2alWLSUk.
Uthamaraj, S. et al., "Fabrication of Small Caliber Stent-grafts Using Electrospinning and Balloon Expandable Bare Metal Stents," Journal of Visualized Experiments, vol. 116, (2016).
Choi, Y-E. et al., "Proangiogenic cells enhanced persistent and physiologic neovascularization compared with macrophages," Experimental & Molecular Medicine, vol. 47, e186, (2015).
Florczyk, U. et al., "Nrf2 Regulates Angiogenesis: Effect on Endothelial Cells, Bone Marrow-Derived Proangiogenic Cells and Hind Limb Ischemia," Antioxidants & Redox Signaling, vol. 20, No. 11, (2014).
Pant, H. R. et al., "Processing and characterization of electrospun graphene oxide/polyurethane composite nanofibers for stent coating," Chemical Engineering Journal, vol. 270, (2015).
Maher, B., "How to Build a Heart," Nature, vol. 499, issue 7456 (2013).
Oh, D. et al., "Peptide-Amphiphile Containing Arginine and Fatty Acyl Chains as Molecular Transporters," Molecular Pharmaceutics, vol. 10(12), (2013).
Li, D. et al., "Electrospinning of Nanofibers: Reinventing the Wheel?," Advanced Materials, vol. 16, No. 14, (2004).
Merritt, S. R. et al., "Electrospinning and Imaging," Advanced Engineering Materals, vol. 14, No. 5, (2012).
Hwang, C-W. et al., "Stem cell impregnated nanofiber stent sleeve for on-stent production and intravascular delivery of paracrine factors," Biomaterals (Jun. 2015).
Spraybase Electrospinning—<<https://www.spraybase.com/electrospinning>>, accessed Feb. 16, 2022.

* cited by examiner

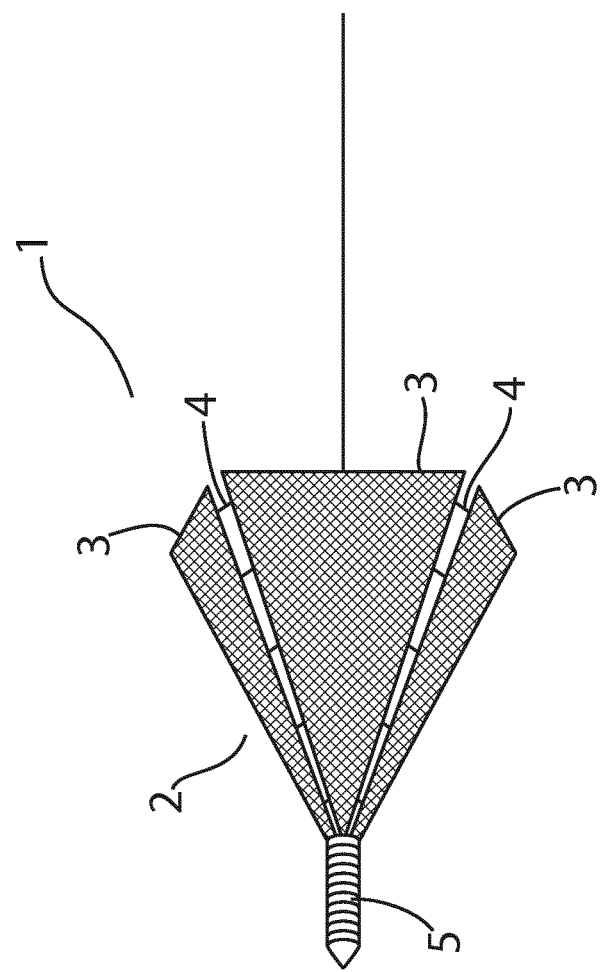

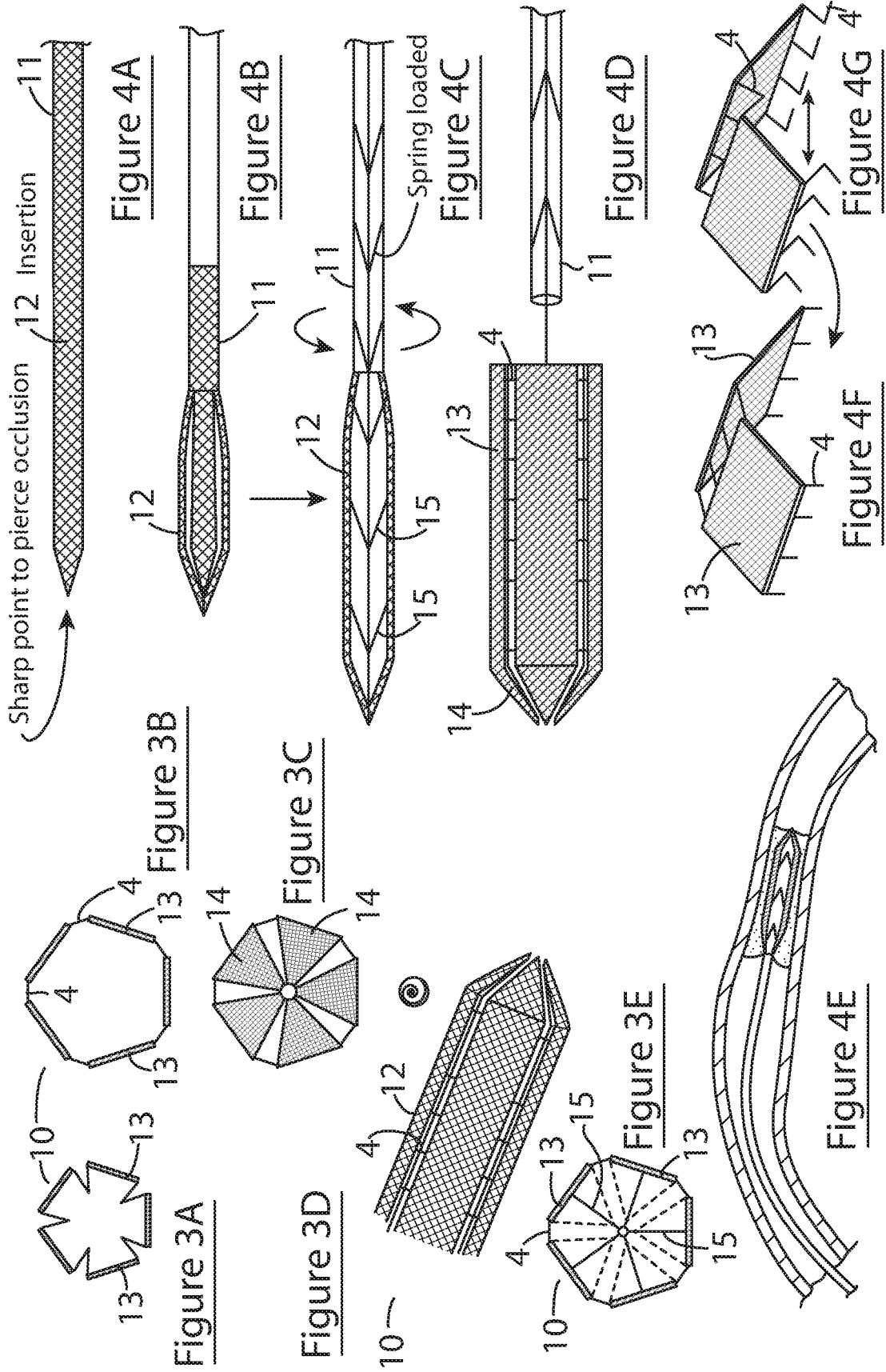

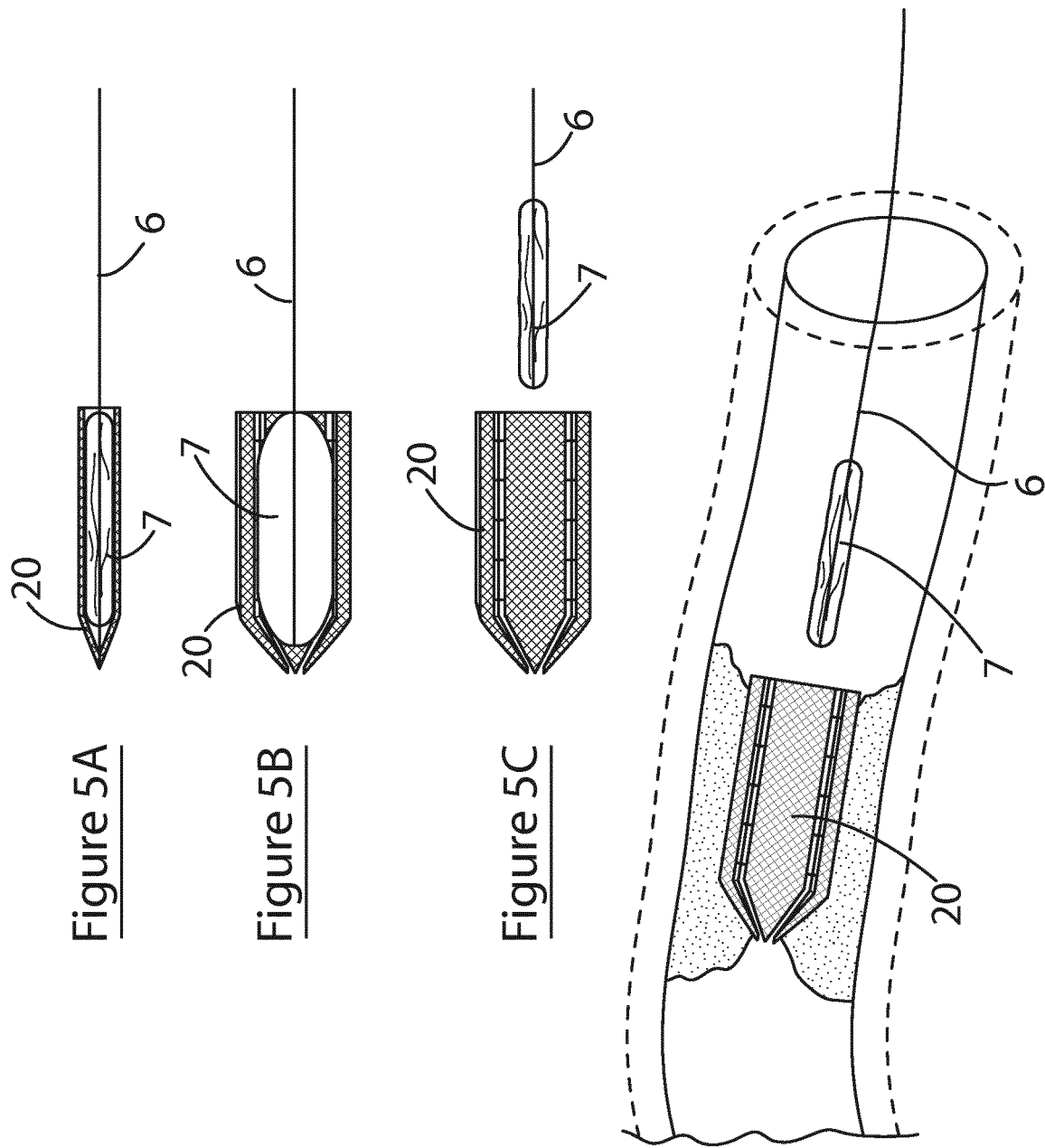

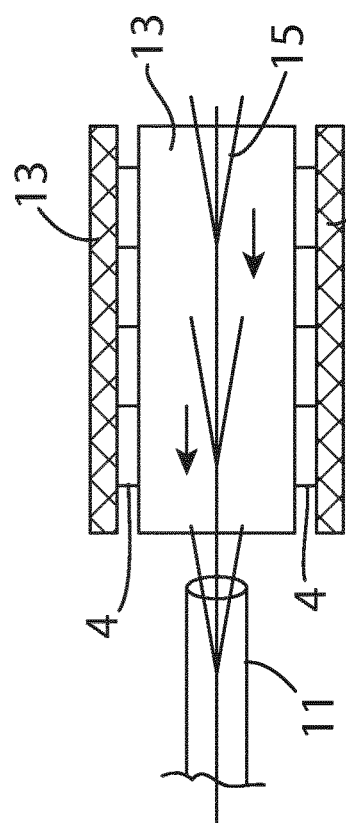
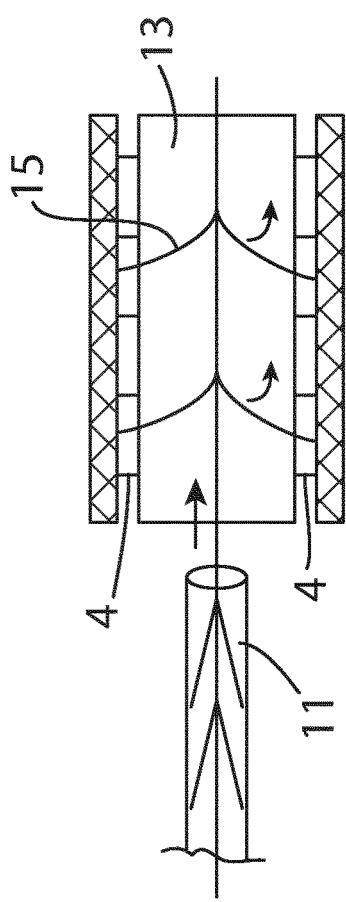
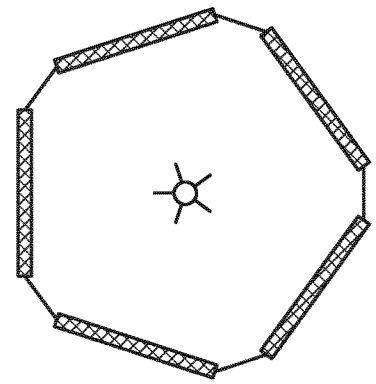
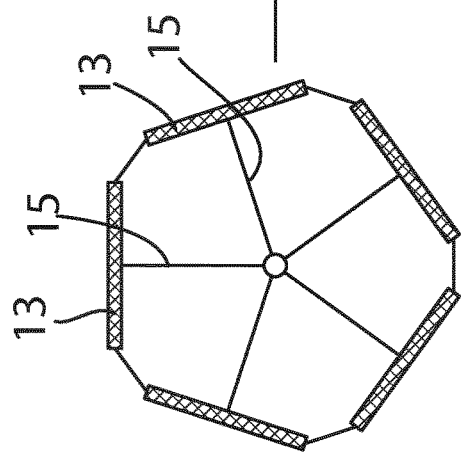
Figure 6A
Figure 6B
Figure 6C

INTRAVASCULAR CELL THERAPY DEVICE

CROSS-REFERENCE TO RELATED APPLICATIONS

This application is the U.S. national stage entry under 35 U.S.C. § 371 of International Application No. PCT/EP2018/054922, filed on Feb. 28, 2018, which claims priority to European Patent Application No. 17158548.2, filed on Feb. 28, 2017.

FIELD OF THE INVENTION

The present invention relates to an intravascular cell therapy device. Also contemplated are methods of treatment of chronic vascular occlusion of coronary or peripheral vasculature, or symptoms of chronic vascular occlusion, that employs the intravascular cell therapy device.

BACKGROUND TO THE INVENTION

Chronic vascular occlusion is currently treated by surgical bypass or less frequently and less successfully by percutaneous coronary intervention (PCI). However, at least 20% of all vascular disease patients remain unsuitable for surgical intervention because of co-morbidities, suboptimal distal artery run off or lack of suitable vascular bypass conduits. These patients may be suitable for a hybrid procedure that can be performed percutaneously (without surgical risks) but also providing microbypass of the occlusion (without the extensive technical, imaging and recurrence limitations of current PCI approaches). This procedure is described in Kumar et al (Biomaterials 35 (2014) 9012-9022), and is based upon use of an intravascular cell therapy device for therapy of VEGF-producing cells to a site of a vascular occlusion causing enhanced vasa-vasora microvessel density and consequent enhanced regional blood flow due to creation of microvascular bypass networks.

SUMMARY OF THE INVENTION

The present invention is in one aspect based on a design of a microbypass intravascular cell therapy device configured to deliver proangiogenic cells to a site of a chronic vascular occlusion for the purpose of developing microvascular bypass networks in continuity from the proximal vessel beyond the occlusion to the distal vessel thereby relieving vascular disease such as ischemia. The device is preferably a biodegradable structure that has a 3-D conformation that allows rapid seeding of proangiogenic cells, facilitates retention of these cells within the device and has a shape that can be altered to allow percutaneous therapy of the device loaded with proangiogenic cells to the vascular occlusion in-vivo by means of an intravascular catheter. The device can be embedded into the vascular wall to allow a microvasculature to develop in continuity from the proximal vessel beyond the occlusion to the distal vessel thus relieving ischemia. The device loaded with proangiogenic cells can be prepared ex-vivo in days—methods of preparation of the cells and seeding of the device is described below and broadly described in Kumar et al. The loaded device can then be delivered to the site of vascular occlusion. In one embodiment, an angiogenic gradient from the site of device placement to the site of distal ischemia facilitates alignment of endothelial cells, pericytes and smooth muscle cells in the surrounding vasculature to create adventitial arterioles that bypass the vascular occlusion and revascularise the distal ischaemic territory. This typically occurs over several weeks. The biodegradable nature of the device reduces the chronic foreign body reaction observed with stainless steel devices and allows angiogenesis and arteriogenesis to progress in-vivo without hindrance by chronic inflammatory processes. The therapy and release mechanism of the device allows rapid deployment into the blunt end of an obstructed artery without the need for a lot of the conventional wires associated with traditional PCI. The device of the invention is for treatment of vascular occlusion, especially chronic vascular occlusion, conditions characterised by vascular occlusion (i.e. peripheral artery disease or atherosclerosis), and symptoms of vascular occlusion (i.e. stroke, myocardial infarction, or ischaemic ulcers).

In a first aspect, the invention provides an intravascular cell therapy device comprising a scaffold that is radially adjustable between a contracted orientation suitable for transluminal delivery to a vascular locus and an expanded orientation, and a typically biodegradable matrix provided on at least a portion of the scaffold that is suitable for seeding with cells.

In another aspect, the invention provides an intravascular cell therapy device comprising a scaffold that is radially adjustable between a contracted orientation suitable for transluminal delivery to a vascular locus and an expanded orientation, and a biodegradable matrix provided on at least a portion of the scaffold that is suitable for seeding with cells.

In another aspect, the invention provides an intravascular cell therapy device comprising a scaffold that is radially adjustable between a contracted orientation suitable for transluminal delivery to a vascular locus and an expanded orientation, and an electrospun polymer matrix provided on at least a portion of the scaffold that is suitable for seeding with cells.

In another aspect, the invention provides an intravascular cell therapy device comprising a scaffold and a matrix provided on at least a portion of the scaffold that is suitable for seeding with cells, in which the scaffold has a piercing tip configured for partial or complete implantation in a plaque.

In another aspect, the invention provides an intravascular cell therapy device comprising a scaffold and a matrix provided on at least a portion of the scaffold that is suitable for seeding with cells, in which the matrix is coated in fibronectin.

In one embodiment, the scaffold is configured to have a distal piercing tip when in a deployed orientation. This allows the scaffold to be at least partly embedded into a plaque and expand within the plaque. This is advantageous because plaque generally comprises microvasculature which is a suitable target for the proangiogenic factors produced by the cells embedded within the device. In addition, embedding the device in the plaque brings the device (and the proangiogenic cells seeded in the device) into close proximity with the plaque microvasculature, as well as the vessel wall microvasculature.

In one embodiment, the distal piercing tip comprises a helical screw formation. This facilitates the device being inserted/embedded into plaque by means of rotation of the device relative to the plaque.

In one embodiment, the scaffold is configured to have a conical shape when deployed. Ideally a distal part of the scaffold is conical. This shape facilitates embedding the device at least partially into a plaque.

In another embodiment, the scaffold is configured to have a partially conical shape when deployed. The term "partially conical" typically means a conical (or frusto-conical) distal part and cylindrical proximal part. This is illustrated in FIGS. 4 and 5. This shape facilitates having a device with a distal end that can be embedded into a plaque, and a proximal end that is exposed proximally of the plaque, whereby the device effects growth of a microbypass network from within the plaque and from within the vessel just proximal of the plaque.

In one embodiment, the device is configured to have a maximum internal diameter of 1-15 mm. In one embodiment (in which the device is optionally for treatment of coronary artery disease), the device is configured to have a maximum internal diameter of 2-5 mm or more preferably 3-4 mm. In one embodiment (in which the device is optionally for treatment of peripheral vascular disease), the device is configured to have a maximum internal diameter of 3-12 mm or more preferably 5-10 mm.

In one embodiment, the scaffold comprises at least one and ideally a plurality of sidewall panels arranged around a longitudinal axis of the scaffold, and adjustable couplings between the panels configured for adjustment between an expanded configuration and a contracted orientation. This arrangement provides sidewall panels of fixed shape and configuration facilitating the retention of cells, and allows radially expansion of the stent without altering the shape of the panels. The couplings may take many forms, for example resiliently deformable members (i.e. springs) or adjustable/foldable members. The connectors may be configured to be biased into an expanded configuration or a contracted configuration. In one embodiment, the scaffold is self-expansible. In one embodiment, the delivery catheter comprises an outer sheath configured for axial movement relative to the scaffold, whereby proximal movement of the sheath exposes the scaffold allowing it to deploy by self-expansion or another deployment mechanism.

In one embodiment, the couplings between the sidewall panels are adjustable between an inwardly folded configuration when the scaffold is in a contracted orientation and an unfolded extended orientation when the scaffold is in an expanded orientation.

In one embodiment, the couplings are configured to lock when adjusted from the folded to unfolded configuration.

In one embodiment, the scaffold has a conical shape, in which the sidewall panels have a generally triangular shape.

In another embodiment, the scaffold has a partially conical shape, and in which each sidewall panel comprises a distal triangular part (i.e. forming the conical part of the scaffold) and a proximal rectangular part (i.e. forming the cylindrical part of the scaffold).

In one embodiment, the distal triangular part and proximal rectangular part of the sidewall panels are integrally formed. In another embodiment, the distal and proximal panels are separate and couple together with a coupling mechanism.

In one embodiment, at least one and ideally all of the sidewall panel comprise a matrix suitable for seeding with cells. This is also referenced herein as a "cell seeding matrix".

In one embodiment, the panels consist essentially of the matrix. In other embodiment, the matrix is formed or coated on the scaffold (for example, by means of electrospinning, especially wet electrospinning, spraying, dipping, depositing, painting, or 3-D printing).

In one embodiment, the matrix is configured to degrade in a vascular environment. In one embodiment, the matrix is configured to degrade over a period of up to 6 months, 5 months, 4 months, 3 months, 2 months or 1 month.

In one embodiment, the matrix is coated in fibronectin.

In one embodiment, the scaffold is configured to degrade in a vascular environment. In one embodiment, the scaffold is configured to degrade over a period of up to 6 months, 5 months, 4 months, 3 months, 2 months or 1 month.

In one embodiment, the device is configured to degrade in a vascular environment. In one embodiment, the device is configured to degrade over a period of up to 6 months, 5 months, 4 months, 3 months, 2 months or 1 month.

In one embodiment, the matrix is provided on a sheath configured to attach to the scaffold. In one embodiment, the sheath is an annular sheath. In one embodiment, the sheath has a distal conical part.

In one embodiment, the matrix has a porosity of at least 60%, 70%, 80% or 90%. In one embodiment, the matrix has a porosity of 85-95%, preferably about 90%. The method of determining % porosity is provided below.

In one embodiment, the matrix has an average pore size of 30-100 microns. In one embodiment, the matrix has an average pore size of 30-60 microns. The method of determining average pore size is provided below.

In one embodiment, the device is configured for transluminal delivery and vascular deployment using a balloon catheter. Thus, the device in a non-deployed, contracted, configuration is nested on a deflated balloon at a distal end of a catheter, the catheter and device are advanced percutaneously to a target site in the vasculature, and ideally embedded into a plaque, and the balloon is then inflated to deploy the device in the plaque. In one embodiment, the device is biased into a contracted orientation, and typically includes a self-locking mechanism configured to lock the device in a deployed orientation once deployed.

In another embodiment, the intravascular cell therapy device comprises an elongated delivery catheter having a proximal end and a distal end, and a coupling mechanism configured to provide releasable coupling between the distal end of the catheter and the scaffold. In one embodiment, the proximal end of the catheter comprises a handle configured for remote actuation of the releasable coupling. In one embodiment, the device comprises a deployment mechanism.

In one embodiment, the coupling mechanism comprises a plurality of radial struts configured to allow limited axial movement between the catheter and the scaffold. In one embodiment, the struts are hingedly connected to the catheter and the scaffold. In one embodiment, the coupling mechanism comprises a deployment mechanism. In one embodiment, the coupling mechanism is configured such that distal movement of the catheter relative to the scaffold causes the scaffold to adapt a contracted orientation and proximal movement of the catheter relative to the scaffold causes the scaffold to adapt an expanded orientation.

In one embodiment, the plurality of radial struts are configured to be released from the scaffold upon axial rotation of the catheter relative to the scaffold. Various way of providing such a rotatably actuated release will be apparent to the person skilled in the art, including the use of re-entrant slots.

In one embodiment, the matrix has an architecture configured to allow rapid seeding cells. In one embodiment, the scaffold has a matrix configured to allow retention of cells within the matrix when the matrix is in a vascular environment and allow diffusion of proangiogenic factors out of the matrix when the matrix is in a vascular environment. Examples of suitable matrices are described in Kumar et al, WO2002/056790, U.S. Pat. Nos. 6,054,122, 6,096,070, 5,824,049, 5,624,411, 5,609,629, 5,569,463, 5,447,724 and 5,464,650.

In another aspect, the invention provides an intravascular cell therapy device according to the invention in which the matrix is seeded with cells (typically living cells). In one embodiment, the cells are proangiogenic cells. In one embodiment, the cells are smooth muscle cells (i.e. induced smooth muscle cells), Induced smooth muscle cells are described in EP3056562. In one embodiment, the cells are mesenchymal stem cells. In one embodiment, the cells have been engineered for expression (typically heterologous expression) of a therapeutic factor, for example an angiogenic factor. Examples of angiogenic factors include VEGF.

In another aspect, the invention relates to a method of treating disease, typically vascular disease, comprising a step of percutaneous delivery of an intravascular cell delivery device of the invention in a contracted delivery orientation to a target site in the vasculature, wherein the matrix has been seeded with cells configured to release a therapeutic factor, and deployment of the device at the target site in the vasculature, whereby the cells retained within the matrix release a therapeutic factor at the site.

The cells may be cells that produce therapeutic factors naturally, or they may be genetically engineered to express or overexpress the therapeutic factors or for heterologous expression of therapeutic factors. Examples of cells include smooth muscle cells, mesenchymal stem cells, Islet cells, endothelial cells, progenitor cells, stem cells, antibody producing cells, immune cells. Examples of therapeutic factors include growth factors, insulin, antibodies, antibody fragments, cytokines, interleukins, interferons, biopharmaceutical products, proteins, nucleic acids.

In another aspect, the invention relates to a method of treating cardiovascular disease, especially coronary artery disease (for example preventing or inhibiting angina, or reducing risk of an ischemic event including a myocardial infarction) in a mammal in need thereof, comprising a step of percutaneous delivery of an intravascular cell delivery device of the invention in a contracted delivery orientation to a site of vascular occlusion, wherein the matrix has been seeded with proangiogenic cells, and deployment of the device at the site of the vascular occlusion, whereby the proangiogenic cells retained within the matrix release proangiogenic factors at the site developing microvascular bypass networks in continuity from the proximal vasculature beyond the occlusion to the distal vasculature thereby increasing regional blood flow.

In one embodiment, the intravascular cell therapy device of the invention has a distal piercing tip, and in which the device is at least partially embedded into the plaque, ideally fully embedded into the plaque. In one embodiment, the device is partially embedded into plaque so that a distal part of the device is embedded into plaque and a proximal end of the device is exposed proximal of the plaque (and ideally the proximal end of the device is disposed in close proximity with the surrounding vessel wall). In one embodiment, the device is deployed after being embedded into the plaque.

In one embodiment, the device is delivered to a target site using a balloon catheter and deployed by inflation of the balloon. In another embodiment, in which the device is operatively and detachably coupled to a delivery catheter, deployment of the device is actuated by proximal axial movement of the catheter relative to the scaffold. In one embodiment, the scaffold is detached from the catheter by rotation of the catheter relative to the scaffold.

In one embodiment, the method includes a step of immersing the scaffold into a liquid containing the proangiogenic cells, to seed the matrix with cells. In one embodiment, the liquid is a cell culture media. In one embodiment, the scaffold is coated in fibronectin prior to seeding with cells.

In another aspect, the invention provides a method of preparing a cell seeded intravascular cell therapy device of the invention. The method comprising the steps of:
coating the device in fibronectin;
incubating the device in a culture of the cells to allow attachment of the cells to the device; and
culturing the cell seeded device in culture media.

In none embodiment, the method includes a step of drying the fibronectin coated device prior to incubation.

In one embodiment, the device is incubated in the cell culture for less than 12 hours, typically 1-4 hours, and ideally about 2 hours.

In one embodiment, the cell seeded device is cultured in culture media for a number of days, for example 1-10, 2-8, 3-7, 4-6 or about 5 days.

In one embodiment, the device is seeded at a density of $1.5 \times 10^6$ cells/cm$^2$ of scaffold, typically in 100 μl of complete media.

In one embodiment, the device is coated in fibronectin at a concentration of 1-20 μg/ml Other aspects and preferred embodiments of the invention are defined and described in the other claims set out below.

BRIEF DESCRIPTION OF THE FIGURES

FIG. 1 is a perspective view of an intracoronary cell therapy device (ICTD) according to a first embodiment of the invention and having a conical shape.

FIGS. 3A to 3E are views of an intracoronary cell therapy device (ICTD) according to a second embodiment of the invention and having a partially conical shape.

FIG. 4A is a side elevational view of the ICTD of FIG. 3 in a retracted, delivery, orientation and showing the scaffold coupled to a delivery catheter FIGS. 4B and 4C are side illustrations of the ICTD in an expanded deployed orientation.

FIG. 4D is an illustration of the ICTD being released from the delivery catheter.

FIG. 4E is a sectional view through a blood vessel showing the ICTD of FIG. 4 being deployed inside a plaque.

FIGS. 4F and 4G illustrate the operation of a folding coupling mechanism between two adjacent panels of the scaffold.

FIG. 5A to 5D illustrate an ICTD similar to that of FIG. 4 but configured to be delivered and deployed using a delivery balloon catheter. FIG. 5A shows the ICTD mounted on a deflated balloon in a contracted delivery orientation, FIG. 5B shows the deployment of the ICTD by inflation of the balloon. FIG. 5C shows the ICTD is an expended orientation and the removal of the deflated balloon, and FIG. 5D shows the deployment of the ICTD in a plaque at a site of chronic vascular occlusion.

FIGS. 6A and 6B show an embodiment of the ICTD of the invention where the scaffold is mechanically coupled to the catheter by radial struts FIG. 6C shows sectional views of the struts providing coupling between the scaffold and the catheter, and how rotation of the catheter (struts) relative to the scaffold effects detachment of the struts from the scaffold.

DETAILED DESCRIPTION OF THE INVENTION

Figure 2A:
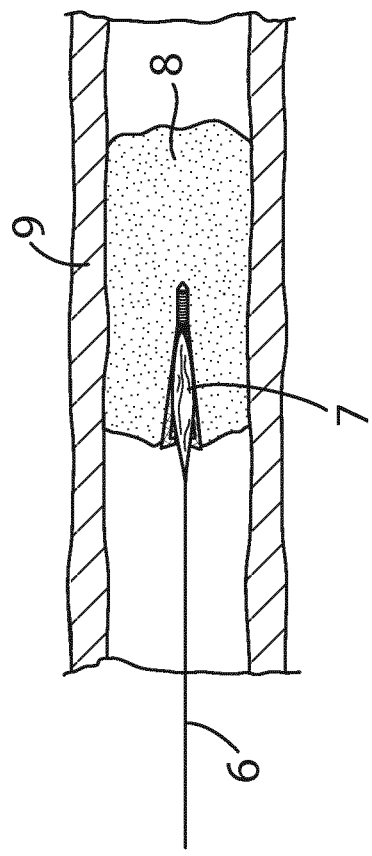
FIGS. 2A to 2C are side views of the ICTD of FIG. 1 being delivered to and deployed within a chronic vascular occlusion.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "vascular disease" is used to define a disease of the vasculature, for example a disease of the arteries, veins and vessels that carry lymph. Examples of vascular is disease of the coronary arteries (coronary artery disease), and disease of vessels that carry blood away from and to the heart (peripheral vascular or artery disease). The term also includes symptoms and conditions resultant from vascular disease, in particular ischaemic disorders such as angina or myocardial infarction (MI) in the case of coronary artery disease, stroke (or transient ischaemic attack—TIA) in the case of vascular disease of the carotid arteries, and claudication, critical limb ischaemia, ischaemic ulcers and gangrene in the case of peripheral vascular/artery disease.

As used herein, the term "treatment" or "treating" refers to an intervention (e.g. the administration of an agent to a subject) which cures, ameliorates or lessens the symptoms of a disease or removes (or lessens the impact of) its cause(s). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

As used herein, the term "intravascular" as applied to the device means a device that is configured for being implanted in the vasculature without causing a significant immune response. "Cell therapy device" means a device that is capable of being seeded with cells and retaining the cells within a matrix on the device during percutaneous therapy and when implanted in the vasculature, while being capable of releasing biological factors expressed by the retained cells in the local vascular environment.

As used herein, the term "matrix" refers to a porous structure suitable for being seeded with cells, retaining the cells within the matrix when implanted in a vascular environment (i.e. without washout), and releasing factors secreted by the cells into the surrounding vascular environment. Examples of suitable matrices are described in Kumar et al, Hwang et al (Biomaterials 2015, June 52), WO2002056790. Hwang at al describe a cell therapy stent sleeve formed from electrospun poly-lactic co-glycolic acid nanofibers seeded with mesenchymal stem cells. Other matrices may be formed from biological materials such as collagen which is formed into a slurry and lyophilised to produce a highly porous scaffold. Examples of cell therapy scaffolds for in-vivo use are described by O'Brien et al (Materials Today, 14, 3 Mar. 20112). Cell therapy scaffolds for use in tissue engineering in the heart are described by Maher et al (Nature Vol. 499 Issue 7456) and Alrefi (Stem Cells Cloning; 2015; 8; 81-101). In one embodiment, the matrix is formed by electrospinning. The coating of medical devices such as stents is described in the literature and provided by the number of companies:
(Electrospin Tech—http://electrospintech.com/covereds-tent.html #.WJh2aIWLSUk);
Spraybase—https://www.spraybase.com/electrospinning/;
Oh et al (Mol Pharm, 2013, Dec. 2, 10(12));
Pant et al (Chemical Engineering Journal, Vol. 270, 15 Jun. 2015);
Uthamaraj et al (J. Vis. Exp. (116) e54731, doi:10.3791/54731 (2016).

The matrix may take the form of a plurality of panels as described herein. The matrix may also take the form of a stent sleeve as described in Hwang et al (2015). In one embodiment, the matrix is formed of a nanofiber mesh. In one embodiment, the nanofiber mesh is formed by electrospinning. In one embodiment, the nanofiber is degradable in a vascular environment. In one embodiment, the matrix comprises an electrospun nanofibre mesh formed of a biodegradable polymer. In one embodiment, the nanofiber comprises PLGA. In one embodiment, the nanofiber comprises polycaprolactone, polyglycolide, plotlactic acid, poly-3-hydroxybutyrate.

As used herein, the term "degrade" or "biodegradable" as applied to the matrix or scaffold means that the matrix or scaffold is made from a material that degrades in a vascular environment, typically within 6 month within the vascular environment. Biodegradable materials for use with stents and implantable devices are well described in the literature, for example, WO2002056790, U.S. Pat. Nos. 6,051,276, 5,879,808, 5,876,452, 5,656,297, 5,543,158, 5,484,584, 5,176,907, 4,894,231, 4,897,268, 4,883,666, 4,832,686 and 3,976,071.

As used herein, the term "electrospinning" or "electrospun" refers to a fibre production method which uses electric force to draw charged threads of polymer solutions or polymer melts up to fibre diameters, typically in the order of some hundreds of nanometres. It is described in the following publications:
Li, D.; Xia, Y. (2004). "Electrospinning of Nanofibers: Reinventing the Wheel?". Advanced Materials. 16 (14): 1151-1170. doi:10.1002/adma.200400719; and
Jump up ^ Merritt, Sonia R.; Agata A. Exner; Zhenghong Lee; Horst A. von Recum (May 2012). "Electrospinning and Imaging". Advanced Engineering Materials. 14 (5): B266-B278. doi:10.1002/adem.201180010.

As used herein, the term "cells" refers to any type of cell that is capable of expressing a therapeutic factor, especially a proangiogenic factor, and includes smooth muscle cells, Islet cells, endothelial cells, progenitor cells, stem cells, mesenchymal stem cells, antibody producing cells, immune cells. The cells may be genetically engineered cells, i.e. engineered to express or overexpress a therapeutic factor. Generally, the cells are living cells. In one embodiment, the cells are proangiogenic cells. Cells may be obtained from tissue of donors or from cell depositories or research Institutions.

As used herein, the term "proangiogenic cells" refers to cells that naturally express, or are engineered to express or overexpress, a proangiogenic factor. Examples include engineered smooth muscle cells described below and the proangiogenic cells described in Choi et al (Experimental & Molecular Medicine 2015, 47; e186) and Florczyk et al (Antioxid Redox Signal April 2014, 10; 20(11)).

As used herein, the term "therapeutic factor" refers to a molecule that has a therapeutic effect in-vivo. Examples include proteins, peptides, nucleic acids including miRNA, siRNA, shRNA and tRNA molecules and derivatives thereof, biopharmaceutical agents, biological growth factors, insulin, antibodies including monoclonal antibodies, antibody fragments, cytokines, interleukins, and interferons.

As used herein, the term "proangiogenic factor" refers to molecules that promote angiogenesis in the body and in particular the formation of new blood vessels from existing blood vessels. Examples include VEGF, FGF, HGF, NPR-1, PDGF, PLGF, and TGF-β.

As used herein, the term "cardiovascular disease" refers to a class of diseases that involve the heart or blood vessels, and includes coronary artery diseases such as angina and myocardial infarction, and cerebrovascular disease (including stroke), heart failure, hypertensive heart disease, cardiomyopathy, heart arrhythmia, peripheral artery disease and venous thrombosis.

As used herein, the term "chronic vascular occlusion" refers to a blockage of a blood vessel causing restricted blood flow to the vessel distal of the blockage. The blockage is generally caused by a plaque, a build-up of cholesterol, fat and calcium which hardens on the inner wall of the blood vessel causing a partial occlusion. A vascular occlusion in the coronary arteries can cause angina and myocardial infarction.

As used herein, the term "releasable coupling mechanism" refers to a coupling mechanism between an implantable device and a therapy catheter for transluminal delivery of the implantable device in the vasculature. The coupling mechanism provides operable connection between the implantable device and the delivery catheter, and is generally remotely actuable to release the implantable device from the delivery catheter once the implantable device has been correctly located in the vasculature. The implantable device may comprise a marker, for example a radiopaque marker, to allow imaging of the device in-vivo during delivery and deployment of the device. The coupling mechanism may be configured for mechanical release or electrocatalytic release. Intravascular devices configured for electrocatalytic release are described in the literature, for example in U.S. Pat. No. 5,925,037. Mechanical coupling mechanisms may include re-entrant locking members, threaded screw engagement members, or any of the loading mechanisms described in US2016166257. In one embodiment, the coupling mechanism may include a plurality of radial struts providing operable connection between a distal end of the delivery catheter and an inside wall of the implantable device. The struts may be connected to the implantable device to allow axial movement of the device without uncoupling, and whereby rotational movement of the delivery catheter relative to the implantable device effects uncoupling of the device from the delivery catheter.

As used herein, the term "deployment mechanism" refers to a mechanism to allow controlled deployment of the device at a desired location in the vasculature or body lumen. Examples of deployment mechanism are well known in the literature, and include self-expansible scaffolds disposed within retaining sheaths (whereby axial retraction of the sheath allows the deployment of the self-expansible scaffold), control arm mechanisms comprising a distal control arm connected to a distal end of the scaffold and a proximal control arm connected to a proximal end of the scaffold, whereby axial movement of one arm relative to the other arm effects expansion or contraction of the scaffold (See for example PCT/IE2014/000005), and radial strut coupling between the device and a control arm whereby movement of the control arm relative to the device effects expansion or contraction of the device (in the manner of the opening and closing of an umbrella).

As used herein, the term "porosity" as applied to a matric material means a measure of the proportion of the matrix material volume composed of open, porous space expressed as a percentage. In simpler terms, it is the percentage pore volume of a porous matrix material. Porosity of a matrix material was determined by the precise measurement of a dry cylinder of a matrix material sample using a mass balance. Using the formula for the volume of a cylinder, πr2h, the density of each sample was calculated by dividing the mass by the volume. Porosity was calculated using the formula 100−[100(ρmatrix/ρmaterial)] where ρmatrix is the density of a given sample and ρmaterial is the weighted density of the matrix constituents.

As used herein, the term "average pore size" refers to the average pore size in the matrix as determined by a linear intercept method. Typically, the matrix has an average pore size of 30-100 microns, preferably 30-60 microns.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Example 1

Figure 2B:
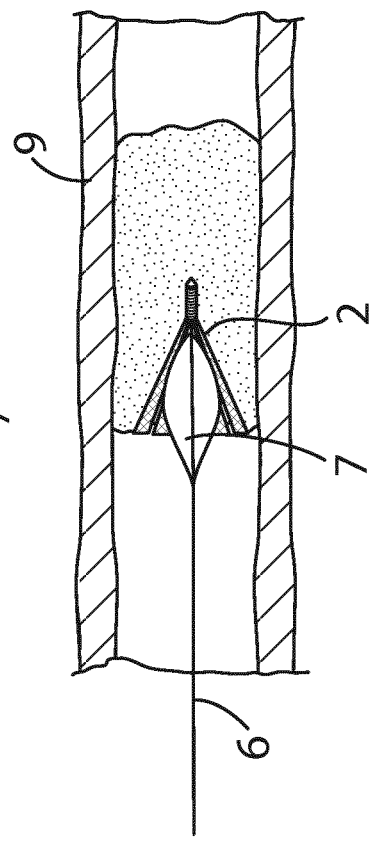
Figure 2C:
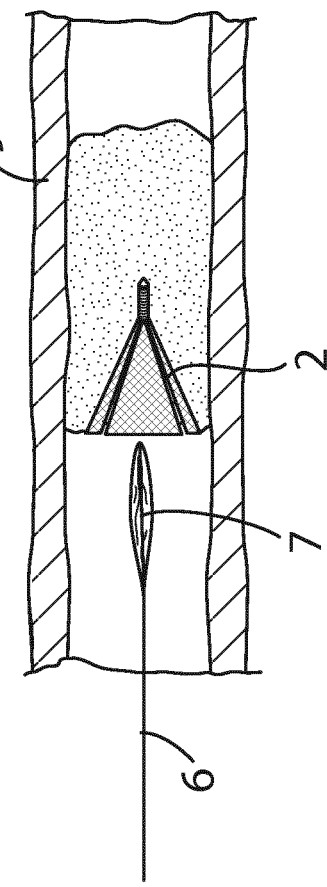
Figure 7B:
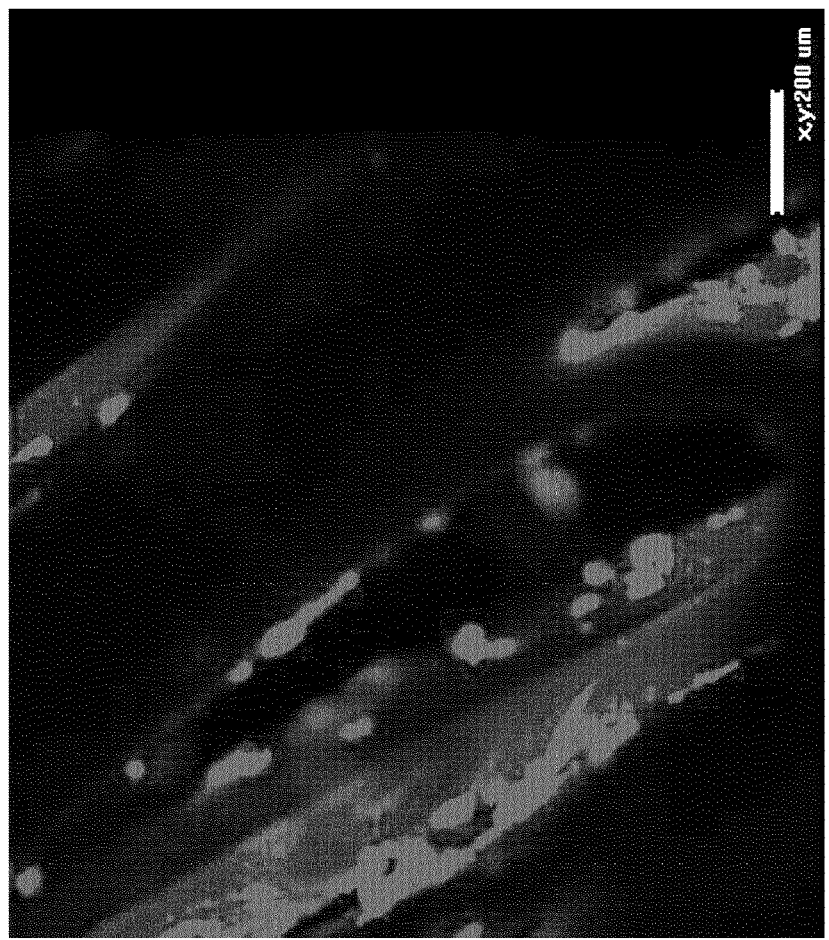
FIG. 7 shows a cell-seeded scaffold of the invention at Day 1 of incubation with no fibronectin coating (FIG. 7A) and with fibronectin coating (FIG. 7B).
Figure 7A:
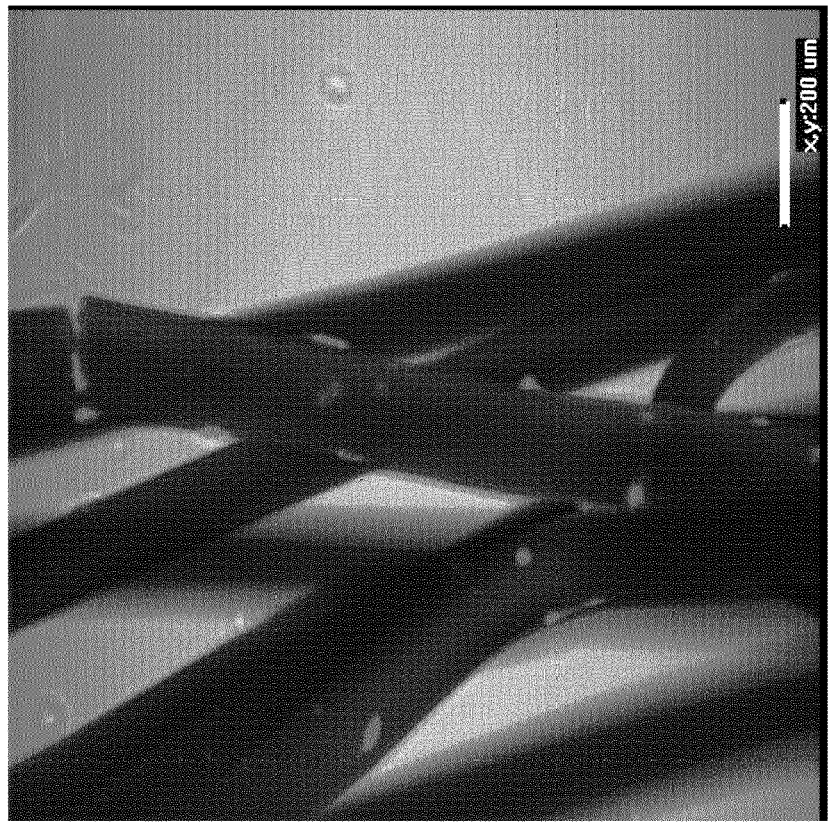
Figure 8:
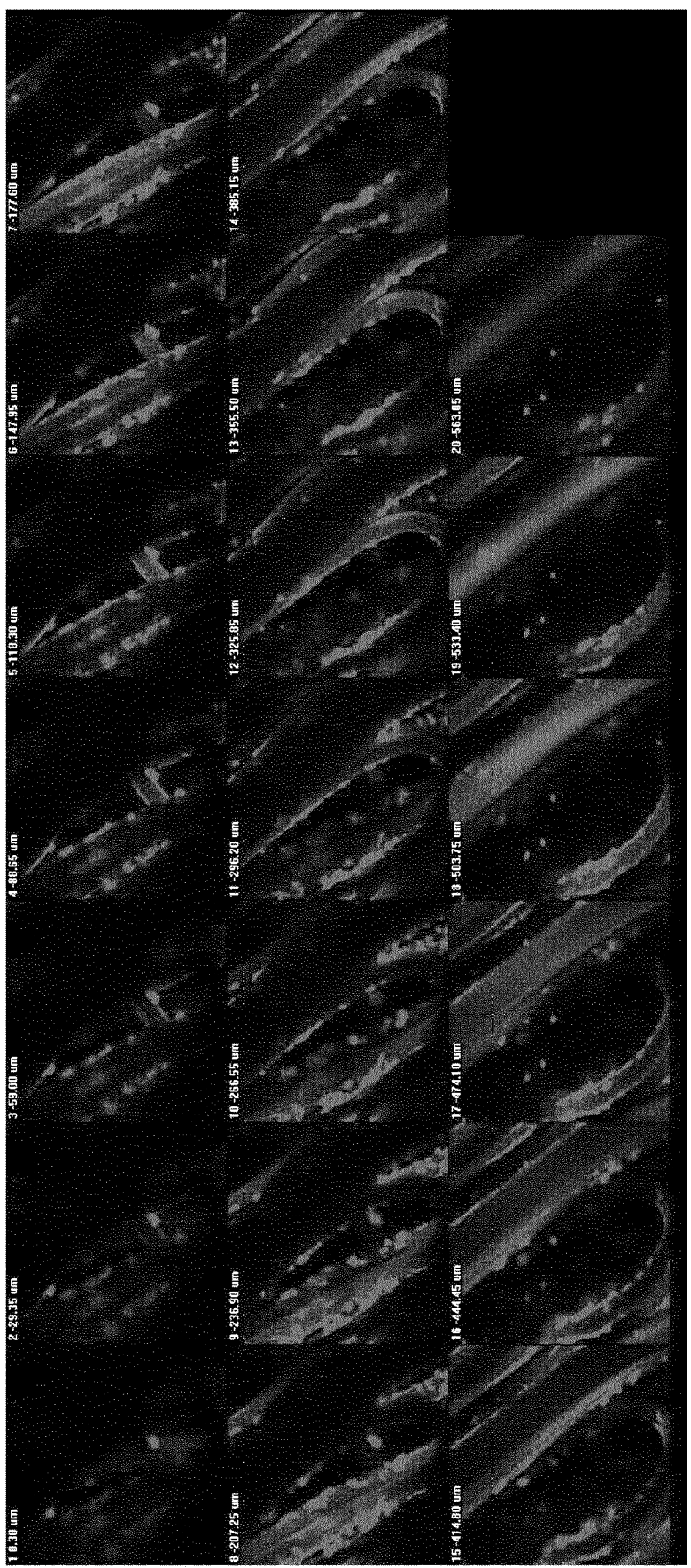
FIG. 8 is a Z stack image through a scaffold of the invention.
Figure 9:
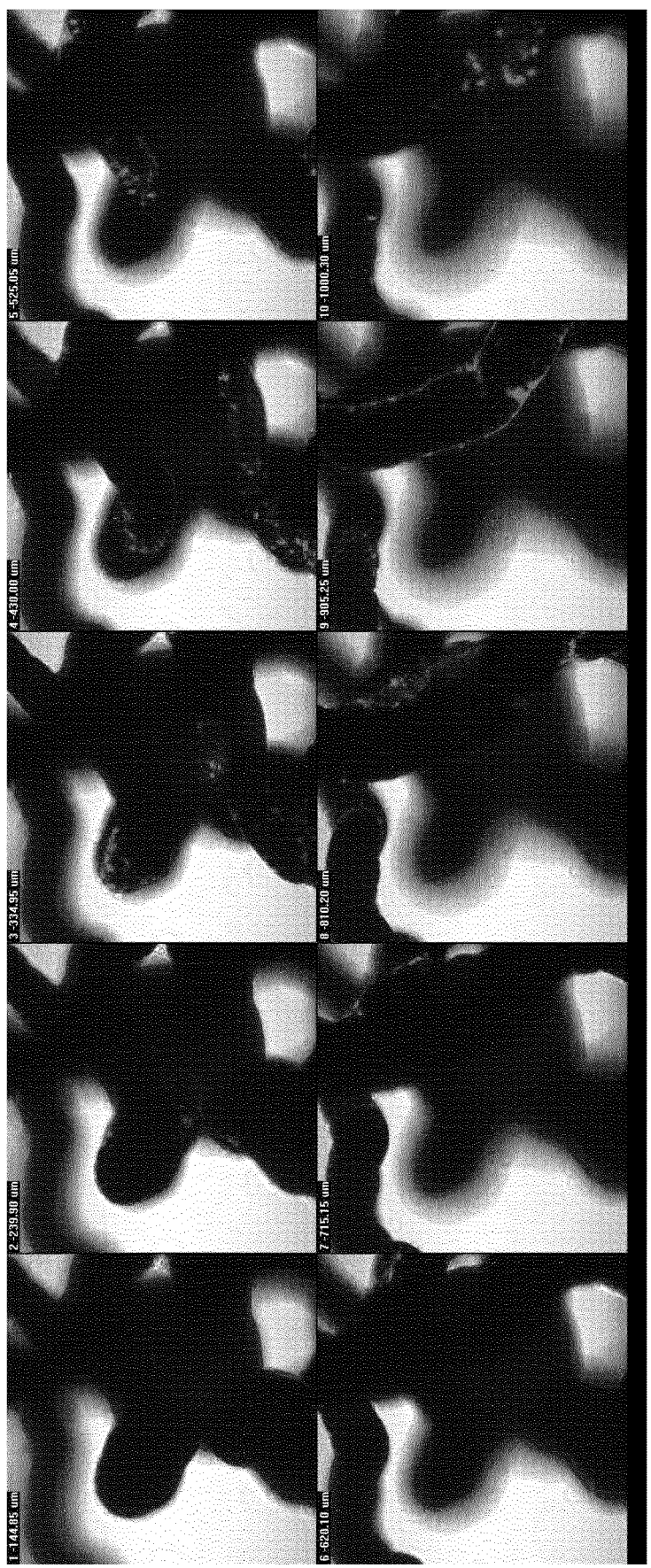
FIG. 9 shows the progressive colonisation of a biodegradable scaffold of the invention with mesenchymal stem cells (Incubation Day 1 to 5).

Referring to FIG. 1, there is illustrated an intravascular cell therapy device (ICTD) of the invention, indicated generally by the reference numerals 1, and comprising a generally conical scaffold body 2 formed by a plurality of sidewall panels 3 of triangular shape and a plurality of adjustable couplings 4 connecting adjacent panels. The scaffold is show in an expanded deployed orientation, with the couplings 4 in an expanded (unfolded) configuration. Although not shown, inward folding of the couplings causes the scaffold to contract and present a smaller profile suitable for percutaneous delivery. The space between adjacent panels when in a deployed orientation will be greater than that illustrated with reference to FIG. 1, with longer couplings, such that when the couplings are folded inwardly, the degree of contraction of the scaffold will be greater. In this embodiment, the couplings are configured to lock when unfolded, thereby locking the scaffold in the deployed configuration In more detail, the panels 3 comprise a PLGA mesh formed by wet electrospinning a PLGA co-polymer. The mesh has a porosity of about 90% and an average pore size of 30-60 microns. The panels of matrix material are sufficiently stiff to be employed without having an underlying supporting scaffold structure. In other embodiments, where the matrix material is less stiff and robust, the matrix material may be formed on an underlying panel shaped scaffold, for example by means of coating. The device also includes a separate threaded piercing tip 5 disposed on a distal end of the scaffold and configured to penetrate plaque in vascular occlusions. This embodiment of the device is configured for delivery using a balloon catheter Referring to FIG. 2, the use of the device of FIG. 1 is illustrated. Referring the FIG. 2A, the device is shown mounted on a balloon 7 of a balloon catheter 6 and embedded into a plaque 8 of a vascular occlusion within a blood vessel 9. In FIG. 2B, the balloon 6 is inflated thereby deploying the device 1 within the plaque 8. FIG. 2C shows the balloon deflated and retracted away from the plaque 8 leaving the device 1 embedded in the plaque.

Example 2

Referring the FIG. 3, a further embodiment of the ICTD device of the invention, and its use, is illustrated, in which parts identified with reference to the previous embodiments are assigned the same reference numerals. In this embodiment, the device 10 comprises a partially conical scaffold 12 and a delivery catheter 11 coupled to the scaffold by means of a releasable coupling mechanism. Referring to FIGS. 3A to 3D, the scaffold 12 comprises five axially elongated sidewall panels 3 having proximal rectangular sections 13 arranged parallel to an axis of the device (forming the cylindrical distal part of the scaffold) and distal triangular sections 14 that taper inwardly towards a distal end of the device (forming the distal conical part of the scaffold). The distal and proximal sections of each panel are hingedly connected to allow for expansion and contraction of the scaffold. The couplings 4 are foldable struts (as shown in FIG. 3A) that unfold and straighten when the scaffold is deployed (FIGS. 3B, 4F and 4G). The panels are formed from a cell delivery matrix material as described in the previous embodiment.

Referring to FIG. 3E, a section view of the scaffold 12 is provided showing the radial struts 15 that provide coupling between the catheter 11 and scaffold 12.

FIGS. 4A to 4D show the operation of the device with the scaffold 12 attached to the catheter in a delivery mode (FIG. 4A), deployment of the scaffold 12 (FIG. 4B), and a sectional view through the device showing the coupling and deployment mechanism which comprises a control arm which extends axially through the delivery catheter 11 and having a plurality of radial struts 15 disposed on a distal end of the control arm providing coupling between the delivery catheter and the scaffold 12. The struts 15 are hingedly connected to both the control arm and scaffold 12, and are configured such that retraction of the control arm relative to the scaffold causes the struts to orient themselves orthogonally to the axis of the control arm, which causes deployment of the scaffold 12 as shown in FIG. 4C. FIG. 4D shows the deployed scaffold 12 and the catheter 11 detached from the scaffold 12. Detachment is achieved by rotation of the control arm (or catheter member and control arm) relative to the scaffold 12, causing the struts to uncouple from the scaffold. FIG. 4E is a sectional view through a blood vessel showing the deployed scaffold 12 attached to the delivery catheter 11 and embedded into a plaque 8.

Example 3

Referring to FIG. 5, a further embodiment of the ICTD device of the invention, and its use, is illustrated, in which parts identified with reference to the previous embodiments are assigned the same reference numerals. In this embodiment, the device 20 comprises a partially conical scaffold 12 configured for delivery and deployment using a balloon catheter 6. Referring the FIG. 5A, the device 20 is shown mounted on a balloon 7 of a balloon catheter 6. In FIG. 5B, the balloon 6 is inflated thereby deploying the device 20 within the plaque 8. FIG. 5C shows the balloon deflated and retracted away from the plaque 8 leaving the device 20 embedded in the plaque.

Example 4

Referring to FIG. 6, the coupling mechanism between the delivery catheter and the scaffold is illustrated in more detail. FIG. 6A shows the therapy catheter 11 coupled to the panels 13 of the scaffold by means of a control arm and a series of radial struts 15. The struts are hingedly connected to the control arm and panels, and are movable from a delivery configuration (not shown) where they lie at a shallow angle to the control arm to a deployed configuration where the struts are disposed nearly orthogonal to the control arm (FIG. 6A). Movement of the struts from the delivery configuration to the deployed configuration is achieved by axial retraction of the control arm relative to the panels. Once the scaffold has been deployed, rotation of the control arm and struts relative to the scaffold effects uncoupling between the control arm and the scaffold (FIG. 6B), allowing retracting of the delivery catheter and control arm and leaving the scaffold implanted in the vasculature.

Example 5

Device Preparation and Seeding of Angiogenic Cells

The device is cleaned by sonication several times in absolute ethyl alcohol, washing in haemo-Sol (4.5 grams/250 ml of water) for 30 min of rocking, rinsing several times in filtered sterile water, washing in absolute alcohol, and gas sterilized. The device matrix is then coated with 10 µg/ml-fibronectin (FN) for 2 hours prior to cell seeding. Briefly liquid phase FN is allowed to dry on to device in a sterile laminar flow unit. Mesenchymal stems cells (p5) are stained with DIL 5 µl/1×10$^6$ cells incubated for 20 minutes at 37° C. and then washed twice with PBS. The device is seeded at a density of 1.5×10$^6$ cells/cm$^2$ scaffold in 100 µl of complete media, and incubated for two hours to allow attachment of cells. 10 mls of culture media is then slowly added to bathe scaffold, which is then incubated for 5 days.

The microbypass stent of the invention is preferably a biodegradable structure that has a 3-D conformation that allows rapid seeding of proangiogenic cells, facilitates retention of these cells within the device and has a shape that can be altered to allow percutaneous delivery of the device loaded with proangiogenic cells to the vascular occlusion in-vivo by means of an intravascular catheter. The device can be embedded into the vascular wall to allow a microvasculature to develop in continuity from the proximal vessel beyond the occlusion to the distal vessel thus relieving ischemia. The device loaded with proangiogenic cells can be prepared ex-vivo in days—methods of preparation of the cells and seeding of the device is broadly described in Kumar et al. The loaded device can then be delivered to the site of vascular occlusion. An angiogenic gradient from the site of device placement to the sire of distal ischemia facilitates alignment of endothelial cells, pericytes and smooth muscle cells in the surrounding vasculature to create adventitial arterioles that bypass the vascular occlusion and revascularise the distal ischaemic territory. This occurs over several weeks. The biodegradable nature of the device reduces the chronic foreign body reaction observed with stainless steel devices and allows angiogenesis and arteriogenesis to progress in-vivo without hindrance by chronic inflammatory processes. The delivery and release mechanism of the device allows rapid deployment into the blunt end of an obstructed artery without the need for a lot of the conventional wires associated with traditional PCI.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. An intravascular cell therapy device comprising a scaffold that is radially adjustable between a contracted orientation suitable for transluminal delivery to a vascular locus and an expanded orientation suitable for embedding in a vascular wall, in which the scaffold comprises a plurality of sidewall panels arranged around a longitudinal axis of the scaffold, and adjustable couplings between the sidewall panels configured for adjustment of the scaffold between the expanded orientation and the contracted orientation, in which each sidewall panel includes a porous matrix formed by electrospinning and configured for being seeded with cells, retaining the cells after implantation in a vascular environment, and degrading in a vascular environment, and live proangiogenic cells loaded into the porous matrix, in which the porous matrix has an average pore size of 30 to 100 microns, and in which the porous matrix is suitable for releasing proangiogenic factors secreted by the live proangiogenic cells into the vascular environment, wherein the adjustable couplings between the sidewall panels are adjustable between an inwardly folded configuration when the scaffold is in the contracted orientation and an unfolded extended configuration when the scaffold is in the expanded orientation, wherein in the inwardly folded configuration the adjustable couplings extend inward from the sidewall panels.

2. An intravascular cell therapy device as claimed in claim 1 in which the scaffold in the expanded orientation comprises a conical distal part around the longitudinal axis of the scaffold.

3. An intravascular cell therapy device as claimed in claim 1 in which the scaffold in the expanded orientation comprises a conical distal part around the longitudinal axis of the scaffold and a cylindrical proximal part around the longitudinal axis of the scaffold.

4. An intravascular cell therapy device as claimed in claim 1 in which the adjustable couplings are configured to bias the scaffold into the expanded orientation.

5. An intravascular cell therapy device as claimed in claim 1 in which the adjustable couplings are configured to lock when adjusted from the inwardly folded configuration to the unfolded extended configuration.

6. An intravascular cell therapy device as claimed in claim 1 in which the scaffold has a conical shape, in which the sidewall panels have a generally triangular shape.

7. An intravascular cell therapy device as claimed in claim 1 in which the scaffold has a conical distal part and a cylindrical proximal part, and in which each sidewall panel comprises a distal triangular part and a proximal rectangular part.

8. An intravascular cell therapy device as claimed in claim 1 and comprising an elongated delivery catheter having a proximal end and a distal end, and a coupling mechanism configured to releasably couple the distal end of the catheter and the scaffold.

9. An intravascular cell therapy device as claimed in claim 1 comprising an elongated delivery catheter having a proximal end and a distal end, and a coupling mechanism configured to releasably couple the distal end of the catheter and the scaffold, in which the coupling mechanism comprises a plurality of radial struts configured to allow limited axial movement between the catheter and the scaffold, whereby distal movement of the catheter relative to the scaffold causes the scaffold to adapt the contracted orientation and proximal movement of the catheter relative to the scaffold causes the scaffold to adapt the expanded orientation.

10. An intravascular cell therapy device as claimed in claim 9 in which the plurality of radial struts are configured to be released from the scaffold upon axial rotation of the catheter relative to the scaffold.

11. An intravascular cell therapy device according to claim 1 in which the porous matrix is coated in fibronectin.

12. The intravascular cell therapy device as claimed in claim 1 in which the scaffold is configured to have a piercing distal tip.

13. The intravascular cell therapy device as claimed in claim 12 in which the longitudinal axis of the scaffold extends through the piercing tip when in the expanded orientation.

14. An intravascular cell therapy device comprising:
a scaffold that is radially adjustable between a contracted orientation suitable for transluminal delivery to a vascular locus and an expanded orientation suitable for embedding in a vascular wall, in which the scaffold comprises
a plurality of sidewall panels arranged around a longitudinal axis of the scaffold, each sidewall panel including a porous matrix formed by electrospinning and having an average pore size of 30 to 100 microns, the pore size configured for being seeded with cells and retaining the cells after being implanted in a vascular environment;
adjustable couplings between the sidewall panels are configured for adjustment of the scaffold between the expanded orientation and the contracted orientation,
wherein, in the expanded orientation, the plurality of sidewall panels together form a conical shape pointing in a delivery direction; and
live proangiogenic cells loaded into the porous matrix.

15. The intravascular cell therapy device as claimed in claim 14 in which the adjustable couplings directly contact the sidewall panels at each end.

16. An intravascular cell therapy device comprising:
a scaffold that is radially adjustable between a contracted orientation suitable for transluminal delivery to a vascular locus and an expanded orientation suitable for embedding in a vascular wall, in which the scaffold comprises
a plurality of sidewall panels arranged around a longitudinal axis of the scaffold, each sidewall panel including a porous matrix formed by electrospinning and having an average pore size of 30 to 100 microns, the pore size configured for being seeded with cells and retaining the cells after being implanted in a vascular environment;
adjustable couplings between the sidewall panels configured for adjustment of the scaffold between the expanded orientation and the contracted orientation,
wherein, in the expanded orientation, the plurality of sidewall panels together converge radially in a delivery direction to a distal-most tip, and the plurality of sidewall panels extend from the distal-most tip to a proximal end of the scaffold; and
live proangiogenic cells loaded into the porous matrix.

17. The intravascular cell therapy device as claimed in claim 16 wherein the distal-most tip includes a piercing member.

18. An intravascular cell therapy device comprising:
a scaffold that is radially adjustable between a contracted orientation suitable for transluminal delivery to a vascular locus and an expanded orientation suitable for embedding in a vascular wall, in which the scaffold comprises
a plurality of sidewall panels arranged around a longitudinal axis of the scaffold, each sidewall panel consisting essentially of a porous matrix formed and being configured for being seeded with cells and retaining the cells after being implanted in a vascular environment;
adjustable couplings between the sidewall panels configured for adjustment of the scaffold between the expanded orientation and the contracted orientation, in which the adjustable couplings between the sidewall panels are adjustable between an inwardly folded configuration when the scaffold is in the contracted orientation and an unfolded extended configuration when the scaffold is in the expanded orientation, wherein in the inwardly folded configuration the adjustable couplings extend radially inward from the sidewall panels.

19. An intravascular cell therapy device as claimed in claim 18
wherein the sidewall panels lack an underlying supporting scaffold structure.

20. An intravascular cell therapy device comprising:
a scaffold that is radially adjustable between a contracted orientation suitable for transluminal delivery to a vascular locus and an expanded orientation suitable for embedding in a vascular wall, in which the scaffold comprises
a plurality of sidewall panels arranged around a longitudinal axis of the scaffold, each sidewall panel comprising a porous matrix formed and being configured for being seeded with cells and retaining the cells after being implanted in a vascular environment;
adjustable couplings between the sidewall panels configured for adjustment of the scaffold between the expanded orientation and the contracted orientation,
in which the adjustable couplings between the sidewall panels are adjustable between an inwardly folded configuration when the scaffold is in the contracted orientation and an unfolded extended configuration when the scaffold is in the expanded orientation, wherein in the inwardly folded configuration the adjustable couplings extend inward from the sidewall panels.

21. An intravascular cell therapy device as claimed in claim 20 in which the adjustable couplings are configured to bias the scaffold into the expanded orientation.

22. An intravascular cell therapy device as claimed in claim 20, each sidewall panel including a porous matrix formed by electrospinning and having an average pore size of 30 to 100 microns.

23. An intravascular cell therapy device as claimed in claim 20, in which the porous matrix is suitable for releasing into the vascular environment proangiogenic factors secreted by live proangiogenic cells loaded into the porous matrix.

* * * * *